US011147923B2

United States Patent
Helmer

(10) Patent No.: US 11,147,923 B2
(45) Date of Patent: Oct. 19, 2021

(54) MEDICAMENT INJECTION DEVICE

(71) Applicant: Sanofi-Aventis Deutschland GMBH, Frankfurt am Main (DE)

(72) Inventor: Michael Helmer, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 251 days.

(21) Appl. No.: 15/778,423

(22) PCT Filed: Nov. 21, 2016

(86) PCT No.: PCT/EP2016/078259
§ 371 (c)(1),
(2) Date: May 23, 2018

(87) PCT Pub. No.: WO2017/089270
PCT Pub. Date: Jun. 1, 2017

(65) Prior Publication Data
US 2018/0339108 A1    Nov. 29, 2018

(30) Foreign Application Priority Data

Nov. 27, 2015  (EP) .................................... 15196690

(51) Int. Cl.
| *A61M 5/24* | (2006.01) |
| *A61M 5/20* | (2006.01) |
| *A61M 5/32* | (2006.01) |
| *A61M 5/142* | (2006.01) |
| A61M 5/34 | (2006.01) |

(52) U.S. Cl.
CPC ........ *A61M 5/2466* (2013.01); *A61M 5/2033* (2013.01); *A61M 5/3202* (2013.01);
(Continued)

(58) Field of Classification Search
CPC ........ A61M 2005/2474; A61M 5/2466; A61M 5/348; A61M 5/3202; A61M 5/2033;
(Continued)

(56) References Cited

U.S. PATENT DOCUMENTS 5,250,037 A    10/1993  Bitdinger
6,210,369 B1 *  4/2001  Wilmot ............... A61M 5/2033
                                                   604/157
(Continued)

FOREIGN PATENT DOCUMENTS

AU    738058     9/2001
CN    102119037  7/2011
(Continued)

OTHER PUBLICATIONS

PCT International Preliminary Report on Patentability in International Appln. No. PCT/EP2016/078259, dated May 29, 2018, 10 pages.
(Continued)

*Primary Examiner* — Lauren P Farrar
*Assistant Examiner* — Hamza A Darb
(74) *Attorney, Agent, or Firm* — Fish & Richardson P.C.

(57) ABSTRACT

A medicament injection device includes a main body configured to receive a medicament cartridge sealed by a first penetrable barrier, a cap assembly including a button cap and a carrier unit, the button cap being rotatable with respect to the carrier unit and wherein the button cap is prevented from being displaced axially in a proximal direction unless the button is rotated into alignment with respect to the carrier unit, a needle carrier releasably coupled to the carrier unit, the needle carrier carrying a needle having a proximal end and a distal end, the needle carrier being releasably coupled to the push button. Subsequent to rotational alignment of the button cap with respect to the carrier unit, the button cap is
(Continued)

axially displaceable in the proximal direction. Axial displacement of the button cap in the proximal direction causes the needle carrier to be displaced axially in the proximal direction.

19 Claims, 5 Drawing Sheets

(52) U.S. Cl.
CPC ....... *A61M 5/3293* (2013.01); *A61M 5/14248* (2013.01); *A61M 5/20* (2013.01); *A61M 5/348* (2013.01); *A61M 2005/2026* (2013.01); *A61M 2005/2407* (2013.01); *A61M 2005/2474* (2013.01); *A61M 2005/3267* (2013.01)

(58) Field of Classification Search
CPC .................. A61M 5/3293; A61M 5/20; A61M 2005/2407; A61M 2005/2026; A61M 2005/3267; A61M 5/14248; A61M 5/3213; A61M 5/3243
See application file for complete search history.

(56) References Cited

U.S. PATENT DOCUMENTS

| | | | |
|---|---|---|---|
| 6,432,088 B1 | 8/2002 | Huang et al. | |
| 2003/0144633 A1* | 7/2003 | Kirchhofer | A61M 5/2033 604/201 |
| 2012/0059333 A1* | 3/2012 | Singhal | A61M 5/001 604/199 |
| 2012/0302989 A1* | 11/2012 | Kramer | A61M 5/2066 604/500 |
| 2015/0272492 A1 | 10/2015 | Schraga | |
| 2016/0000992 A1* | 1/2016 | Steel | A61M 5/002 604/198 |

FOREIGN PATENT DOCUMENTS

| | | | |
|---|---|---|---|
| CN | 104428020 | 3/2015 | |
| EP | 2740503 A1 * | 6/2014 | ............. B65D 85/24 |
| JP | S62-197070 | 8/1987 | |
| JP | H08-010326 | 1/1996 | |
| JP | 2002-035127 | 2/2002 | |
| WO | WO 99/30759 | 6/1999 | |
| WO | WO 2007/131013 | 11/2007 | |
| WO | WO 2009/150078 | 12/2009 | |
| WO | WO 2014/001319 | 1/2014 | |

OTHER PUBLICATIONS

PCT International Search Report and Written Opinion in International Appln. No. PCT/EP2016/078259, dated Feb. 22, 2017, 15 pages.

* cited by examiner

MEDICAMENT INJECTION DEVICE

CROSS REFERENCE TO RELATED APPLICATIONS

The present application is the national stage entry of International Patent Application No. PCT/EP2016/078259, filed on Nov. 21, 2016, and claims priority to Application No. EP 15196690.0, filed on Nov. 27, 2015, the disclosures of which are expressly incorporated herein in entirety by reference thereto.

TECHNICAL FIELD

The present disclosure relates to medicament injection devices.

BACKGROUND

Medicament injection devices can take various forms. One form uses a syringe, where medicament is stored in a hollow cylinder, typically formed of glass. The medicament is sealed from the environment with a plunger moveable within the cylinder, and a needle fluidly connected to the syringe's distal end. The needle must remain capped in order to maintain the medicament under sterile conditions.

Another form of injection device uses a cartridge instead of a syringe, the cartridge having a distal seal instead of the syringe's needle. Typically a patient connects a double-ended needle to the cartridge before injection, thereby piercing the cartridge's seal with the proximal tip of the double-ended needle.

While a cartridge can provide handling and storage advantages relative to syringes, they are not without shortcomings. For example, the attachment of a needle to the cartridge requires an additional step. This step can be problematic for patients with limited dexterity, poor coordination, or who have lost a degree of sensation in their hands. Even with such disadvantages, in certain situations it is desirable to provide an injection device in which the needle is kept separate from the medicament until such time as the patient wishes to commence the injection. The injection device described herein aims to overcome one or more problems associated with prior devices.

SUMMARY

A first embodiment provides a medicament injection device comprising a main body configured to receive a medicament cartridge sealed by a first penetrable barrier; a cap assembly comprising a button cap and a carrier unit, wherein the button cap is dimensioned to fit over the carrier unit, the button cap being rotatable with respect to the carrier unit and wherein the button cap is prevented from being displaced axially in a proximal direction unless the button is rotated into alignment with respect to the carrier unit, a needle carrier releasably coupled to the cap assembly, the needle carrier carrying a needle having a proximal end and a distal end, wherein, subsequent to rotational alignment of the button cap with respect to the carrier unit, the button cap is axially displaceable in the proximal direction, wherein axial displacement of the button cap in the proximal direction causes the needle carrier to be displaced axially in the proximal direction; and wherein, subsequent to axial displacement of the button cap in the proximal direction, the button cap and carrier unit of the cap assembly are separable from the main body in a distal direction.

The device may further comprise a medicament cartridge holder for holding the medicament cartridge, the medicament cartridge holder having a fixing part for fixing the needle carrier to the medicament cartridge subsequent to axial displacement of the needle carrier in the proximal direction.

The button cap and carrier unit may each have alignment marks thereon to provide a user indication of rotational alignment of the button cap with respect to the carrier unit.

The carrier unit may comprise a pivotable latch arranged to release the cap assembly from the main body of the device upon actuation.

The button cap comprises a bore for receiving the distal end of the needle and the carrier unit comprises a bore for receiving the proximal end of the needle prior to axial displacement of the button cap.

The bore for receiving the proximal end of the needle may be sealed at a proximal end thereof by a second penetrable barrier.

The button cap and carrier unit may comprise a locking arrangement so that, subsequent to axial displacement of the button cap with respect to the carrier unit, the button cap and carrier unit are fixed with respect to each other.

The locking arrangement may comprise at least one protruding member and at least one respective cooperating recess located on respective surfaces of the button cap and carrier unit.

The device may contain a medicament cartridge sealed by the first penetrable barrier, wherein axial movement of the needle carrier in the proximal direction causes a proximal end of the needle to pierce the first penetrable barrier.

The medicament cartridge may contain a medicament.

The device may be an auto-injector device.

A second embodiment provides a method of operating the medicament injection device having a cap assembly, the method comprising rotating a button cap into alignment with a carrier unit, wherein the button cap is dimensioned to fit over the carrier unit, displacing the button cap in a proximal axial direction with respect to the carrier unit, thereby causing a needle to penetrate a cartridge septum; removing the button cap and the carrier unit of the cap assembly by pulling the cap assembly in a distal axial direction opposite to the proximal axial direction.

The method may further comprise actuating a pivotable latch to release the cap assembly from the main body of the device.

Rotating a button cap into alignment with a carrier unit may comprise aligning respective alignment marks provided on the button cap and the carrier unit.

BRIEF DESCRIPTION OF THE DRAWINGS

Exemplary embodiments of the present disclosure are described with reference to the accompanying drawings, in which.

DETAILED DESCRIPTION

Figure 1:
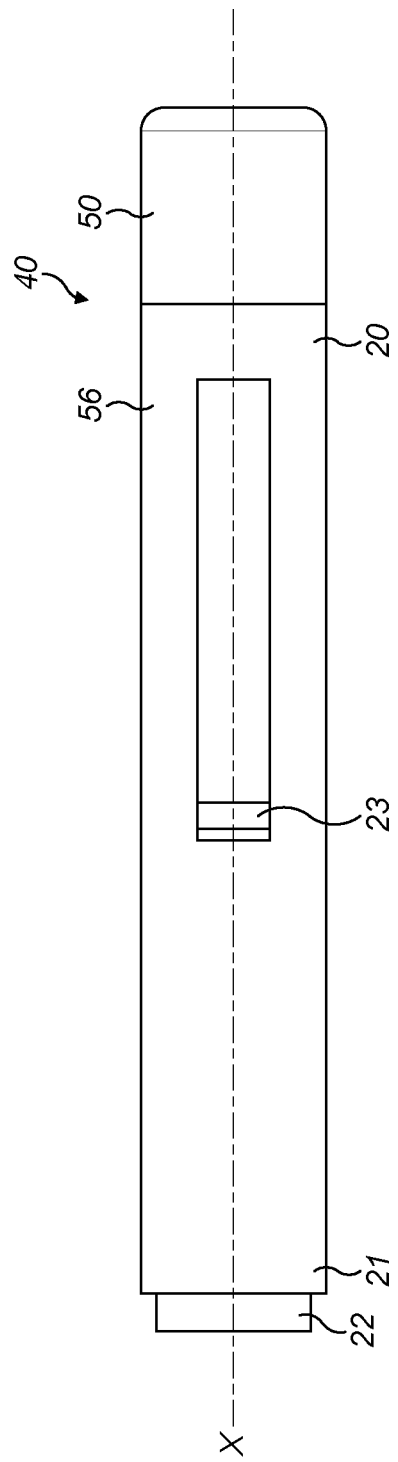
FIG. 1 is a side-on view of an auto-injector device according to an embodiment of the disclosure.

Embodiments of the present disclosure provide a mechanism for inserting a needle of an injection device into a cartridge containing a medicament for injection by a patient or care giver. The mechanism allows the medicament cartridge to remain sealed until such time as the user wishes to commence the injection. Automating a mechanism for inserting the needle into the medicament cartridge also reduces the amount of handling of the needle by the user prior to the injection. Indeed, in some embodiments described below, the user does not touch the needle when the needle is inserted into the medicament cartridge.

In embodiments of the disclosure the needle is initially coupled to a cap of the device and is isolated from the sealed medicament cartridge during storage (i.e. after manufacture and before use). By pushing the cap, the use causes the needle to become fixed to the medicament cartridge and to disengage from the cap. The cap can only be pushed once it has been rotated into alignment. This prevents the cap being pushed accidentally. The cap can then be removed. As a result, the needle is in fluid communication with medicament and the injection may be commenced.

The steps of storing the device and subsequently inserting the needle into the medicament cartridge can be performed without exposing the needle.

Embodiments provide a needle cap triggered piercing unit or rather a method for auto-injectors where a needle will be connected to a cartridge when the user activates a button on a needle cap prior to the cap being removed (before injection or using the device).

The arrangement provides needle safety and seals the sterilised needle against environmental conditions.

The user may be unable to remove the cap before the cap has been aligned and pushed which causes the piercing procedure is carried out. The cap will be released by the mechanism when the needle has reached its end position.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device. The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 40 is shown in FIG. 1. Device 40, as described above, is configured to inject a medicament into a patient's body. Device 40 includes a main body 56 which typically contains a reservoir containing the medicament to be injected (e.g., a syringe) and the components required to facilitate one or more steps of the delivery process. Device 40 can also include a cap assembly 50 that can be detachably mounted to the main body 56. Typically a user must remove cap 50 from main body 56 before device 40 can be operated.

As shown, main body 56 is substantially cylindrical and has a substantially constant diameter along the longitudinal axis X. The main body 56 has a distal region 20 and a proximal region 21. The term "distal" refers to a location that is relatively closer to a site of injection, and the term "proximal" refers to a location that is relatively further away from the injection site.

Device 40 can also include a needle sleeve 55 coupled to main body 56 to permit movement of sleeve 55 relative to main body 56. For example, sleeve 55 can move in a longitudinal direction parallel to longitudinal axis X. Specifically, movement of sleeve 55 in a proximal direction can permit a needle 17 to extend from distal region 20 of main body 56.

Insertion of needle 17 can occur via several mechanisms. For example, needle 17 may be fixedly located relative to main body 56 and initially be located within an extended needle sleeve 55. Proximal movement of sleeve 55 by placing a distal end of sleeve 55 against a patient's body and moving main body 56 in a distal direction will uncover the distal end of needle 17. Such relative movement allows the distal end of needle 17 to extend into the patient's body. Such insertion is termed "manual" insertion as needle 17 is manually inserted via the patient's manual movement of main body 56 relative to sleeve 55.

Another form of insertion is "automated," whereby needle 17 moves relative to main body 56. Such insertion can be triggered by movement of sleeve 55 or by another form of activation, such as, for example, a button 22. As shown in FIG. 1, button 22 is located at a proximal end of main body 56. However, in other embodiments, button 22 could be located on a side of main body 56.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 40 is activated. A proximal end of the drive spring can be fixed within proximal region 21 of main body 56, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 55 or main body 56. Retraction can occur when sleeve 55 moves distally as a user removes device 40 from a patient's body. This can occur as needle 17 remains fixedly located relative to main body 56. Once a distal end of sleeve 55 has moved past a distal end of needle 17, and needle 17 is covered, sleeve 55 can be locked. Such locking can include locking any proximal movement of sleeve 55 relative to main body 56.

Another form of needle retraction can occur if needle 17 is moved relative to main body 56. Such movement can occur if the syringe within main body 56 is moved in a proximal direction relative to main body 56. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and main body 56 can be locked with a locking mechanism. In addition, button 22 or other components of device 40 can be locked as required.

Figure 2A:
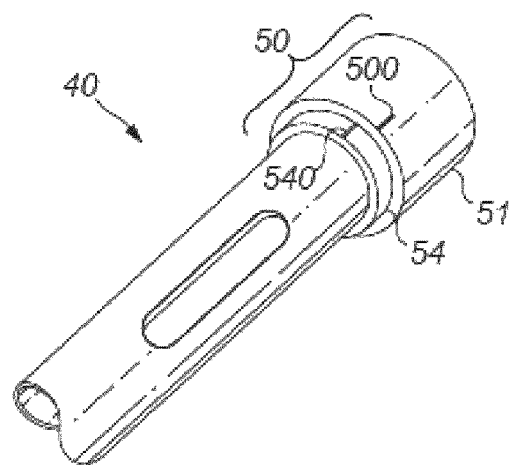
FIGS. 2A-D are perspective views of the auto-injector device in different stages of use.

FIG. 2A shows a device 40 in its original state. This is the state of the device after it has been assembled and packaged. The device 40 is in this state when the user removes the device 40 from the package. The device 40 has a cap assembly 50 comprising a button cap 51 and a carrier unit 54. The button cap 51 has an alignment mark 500 provided on a surface thereof and the carrier unit 54 has an alignment mark 540 on a surface thereof.

Figure 2B:
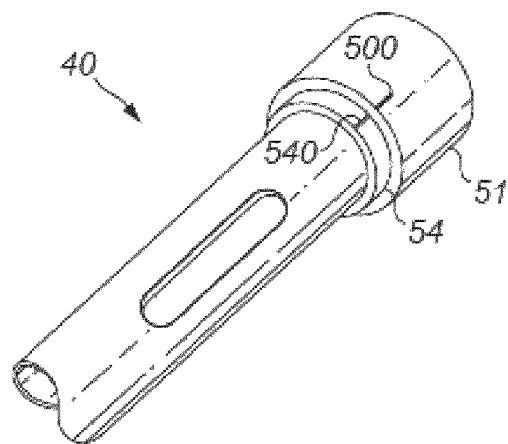

FIG. 2B shows the device 40 after button cap 51 has been rotated with respect to the carrier unit 54 so that the alignment mark 500 is brought into alignment with the alignment mark 540. This provides a visual indication to the user that the cap button cap 51 may be pushed.

Figure 2C:
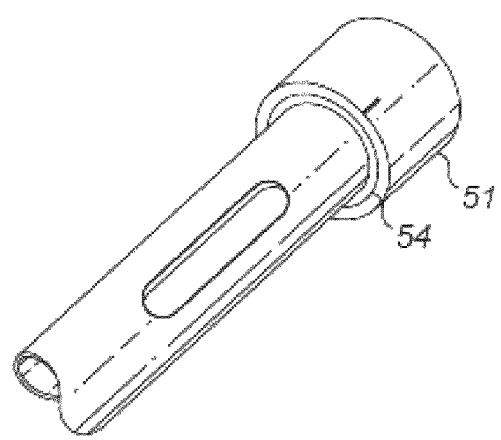

FIG. 2C shows the device 40 after the button cap 51 has been pushed. The needle 17 has been inserted into the medicament cartridge 19.

Figure 2D:
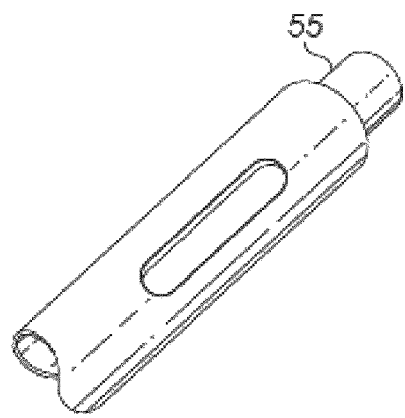

FIG. 2D shows the device 40 after the cap 50 has been removed. The needle 17 has been inserted into the medicament cartridge 19. The needle 17 is not visible in FIG. 2D because a needle sleeve 55 is obstructing the view of the needle 17.

Figure 3:
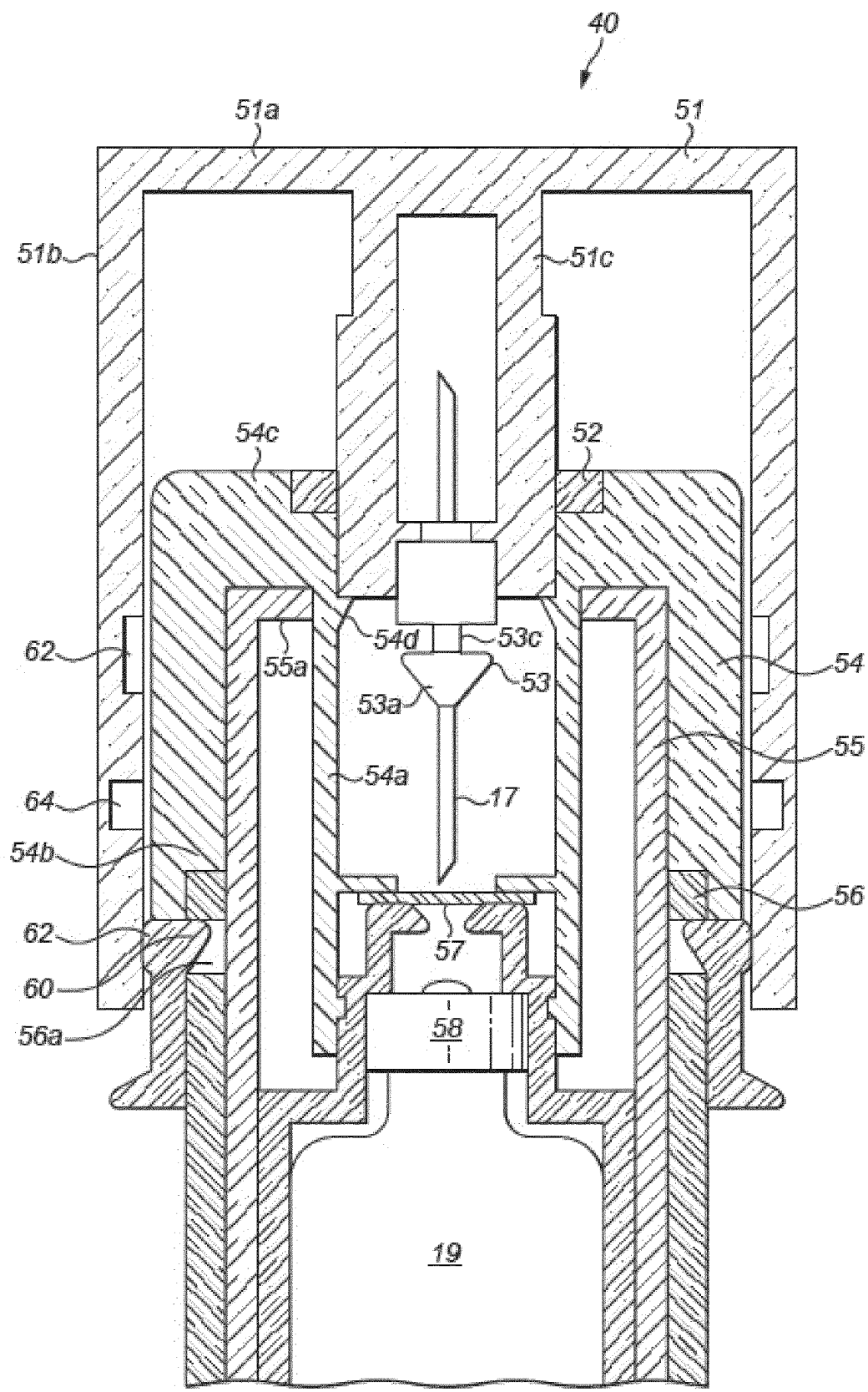
FIG. 3 is a cross sectional view of a distal end of the auto-injector device at the stage shown in FIG. 2A.

FIG. 3 shows a device 40 according to a second embodiment of the disclosure. A cap assembly 50 comprises a button cap 51 and a carrier unit 54. In the storage phase, the button cap 51 and carrier unit 54 are movable rotationally with respect to each other. Once aligned rotationally, the button cap 51 and carrier unit 54 are movable axially with respect to each other as the user pushes the button cap 51.

The cap assembly 50 comprises a button cap 51. The button cap 51 is a generally cylindrical cup. The button cap 51 has a distal end wall 51a, and a curved side wall 51b perpendicular to the distal end wall 51a. The button cap 51 has a diameter greater than the diameter of the carrier unit. As such, the button cap 51 is dimensioned to fit over the carrier unit 54. The button cap 51 has a needle receiving part 51c for receiving the distal end of the needle 17 when the device 40 is in the storage phase. The needle receiving part 51c is a tubular wall extending from the distal end wall 51a and open at the proximal end thereof to receive the distal end of the needle 17.

The needle 17 is held by a needle carrier 53. The needle carrier 53 has a tapered proximal end 53a to engage with the medicament cartridge holder 59 subsequent to the user pushing the button cap 51. The needle carrier 53 has a cylindrical end 53b at the distal end that forms an interference fit with the tubular needle receiving part 51c during the storage phase. The interference fit is sufficiently strong to hold the needle carrier 53 during the storage stage but sufficiently weak to release the needle carrier 53 when the cap is removed. The needle carrier 53 has a circumferential groove 53c between the tapered end 53a and the cylindrical end 53b.

A sealing ring 52 made from rubber or any other suitable material for sealing the compartment in which the proximal end of the needle 17 is stored at the distal end of the compartment may be provided at the interface between the receiving part 51c and the carrier unit 54. A sealing surface may be incorporated into the surface of the cap 51 and carrier unit 54 as an alternative to the sealing ring 52.

A foil or other sealing material 57 may be provided to seal the proximal end of the compartment in which the proximal end of the needle 17 is stored.

The carrier unit 54 is an element of the cap assembly having inner 54a and outer 54b tubular parts, coaxial with respect to each other and connected to each other by a radial part 54c. The inner tubular part 54a is located inside the needle sleeve 55 and extends from the radial part 54c to the medicament cartridge and defines the side wall of the compartment in which the proximal end of the needle 17 is stored during the device storage phase. The outer tubular part 54b extends from the radial part 54c between the button cap side wall 51b and the main body 56 and needle sleeve 55.

The proximal end of the needle receiving part 51c is arranged to sit inside the inner tubular part 54a. The inner surface of the inner tubular part 54a is provided with button cap engagement blocking members 54d to support the proximal end of the needle receiving part 51c of the push button 51 and to prevent axial movement of the button cap 51 with respect to the carrier unit 54 until the button cap 51 and the carrier unit 54 are rotatably aligned.

The device 40 is provided with a substantially tubular needle sleeve 55 having an inwardly flanged distal end 55a.

The proximal end of the outer tubular part 54b comprises a latch member 60 pivotally attached to the remainder of the outer tubular part 54b. The latch member 60 comprises an inwardly extending cooperating ridge 60a located on an inwardly facing surface of the latch member 60. The latch member 60 has an outwardly extending cooperating ridge 60b located on an outwardly facing surface of the latch member 60.

Figure 5:
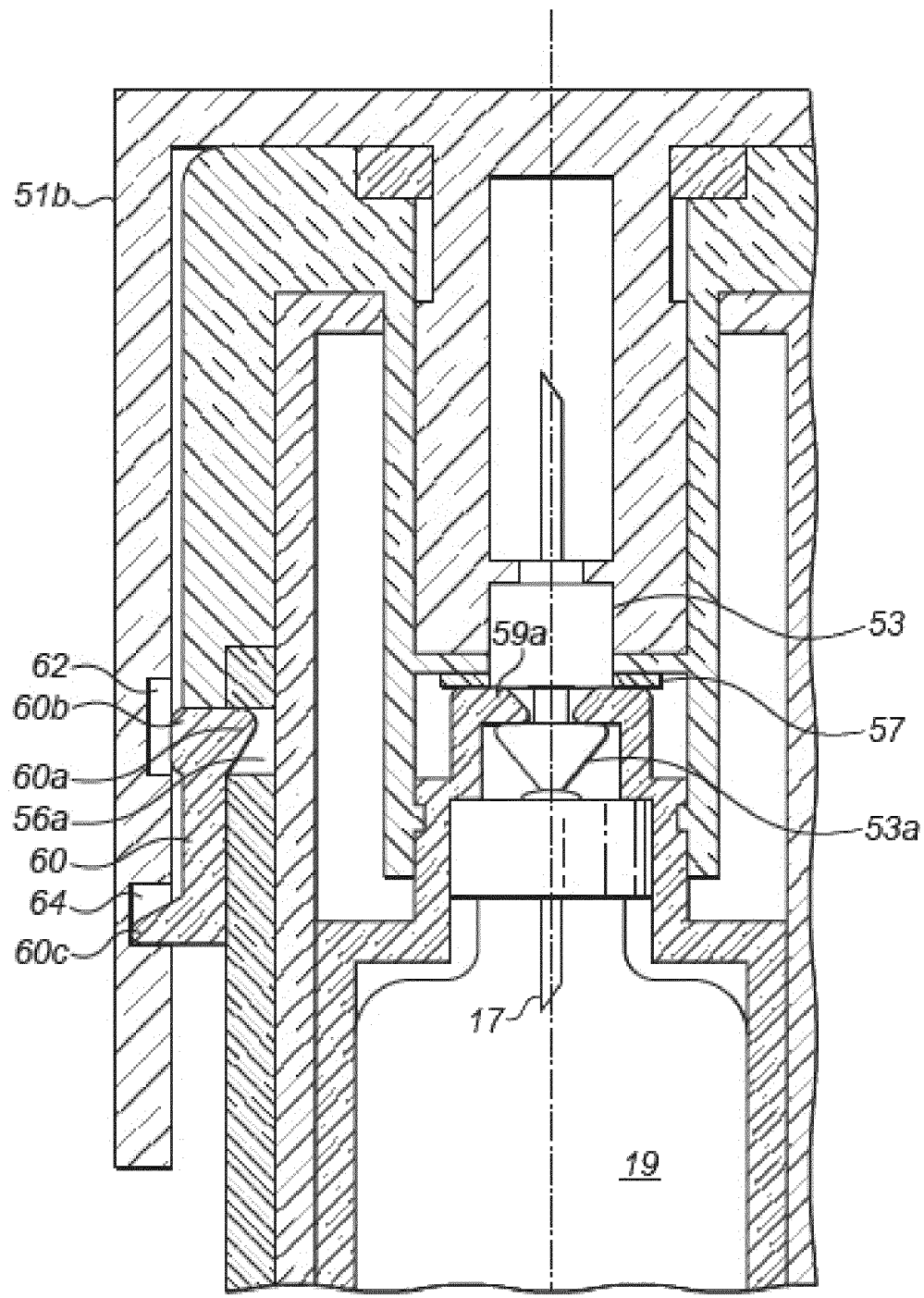
FIG. 5 is a cross sectional view of a distal end of the auto-injector device at the stage shown in FIG. 2C.

As shown in FIG. 5, the inwardly extending cooperating ridge 60a is arranged to engage with a circumferential groove 56a located in the wall of the main body 56.

The outwardly extending cooperating ridge 60b is arranged to engage with a circumferential groove 62 extending around the inner facing surface of side wall 51b subsequent to the button cap 51 being pushed.

The proximal end of the latch member 60 is provided with a locking arm 60c. The locking arm 60c is arranged to engage with a circumferential groove 64 extending around the inner facing surface of side wall 51b subsequent to the button cap 51 being pushed. As such, the button cap 51 is arranged to become fixed to the carrier unit 54 after the button cap 51 has been depressed.

A cartridge holder 59 is provided which provides the interface between the needle carrier 53 and the medicament cartridge 19.

The carrier unit 54 is arranged relative to the main body 56 so that they are fixed together during the storage phase of the device 40. An anti-rotation lock (not shown) is provided to prevent co-rotation of the carrier unit 54 or main body 56 when the user twists the button cap 51 to align with the carrier unit, as shown in FIG. 2B.

In use, the user may remove the device 40 from a package in which the device is stored. Prior to commencing the injection, the needle 17 needs to be inserted into the medicament cartridge 19 and the cap needs to be removed. A device 40 in the storage state is shown in FIG. 2A.

Figure 4:
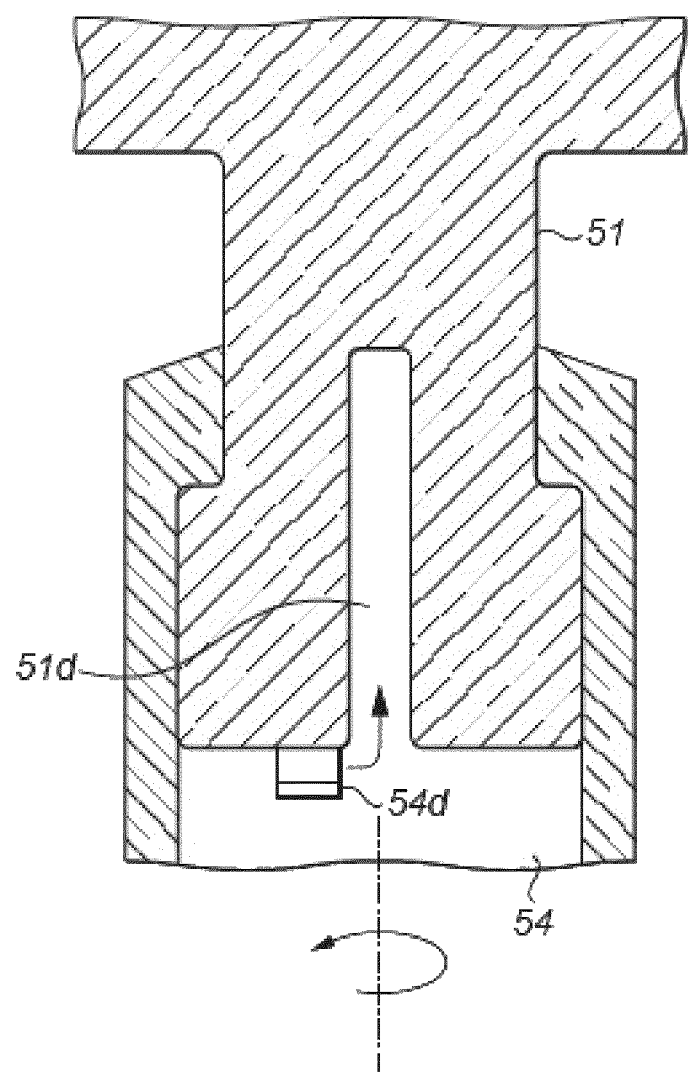
FIG. 4 is an exploded cross sectional view of part of the distal end of the auto-injector device during the stages shown in FIGS. 2A and 2B.

The user rotates the cap 51 so that the mark 500 on the button cap 51 is aligned with the mark 540 on the carrier unit 54, as shown in FIG. 2B. The rotation of the button cap 51 causes the button cap engagement blocking members 54d to align rotationally with slots 51d provided in the outer face of the tubular wall of the needle receiving part 51c of the button cap 51, as shown in FIG. 4.

Once the button cap 51 and carrier unit 54 have been aligned rotationally, the button cap 51 can be pushed axially towards the proximal end of the device 40, as shown in FIG. 5. The button cap 51 is pushed so that it moves axially towards the proximal end of the device 40. The axial movement of the button cap 51 causes the needle carrier 53 and needle 17 to move axially towards the medicament cartridge 19. The proximal end of the needle 17 breaks the foil 57 and pierces the septum of the medicament cartridge. The tapered end 53a of the needle carrier 53 pushes past a distal end flange 59a of the medicament cartridge holder 59. As the needle 17 pierces the sealing foil 57, the foil 57 is displaced by the tapered part 53a of the needle carrier 53. The distal end flange 59a engages with the circumferential groove 53c of the needle carrier 53. As such, the needle carrier is fixed to the medicament cartridge 19.

After the button cap 51 has moved axially to the position shown in FIG. 5, the user can remove the cap assembly from the device 40 by pulling the cap assembly in an axial direction. The ridge 60b is engaged with the groove 62 and the locking arm 60c is engaged with the groove 64, thereby fixing the button cap 51 to the carrier unit 54.

The user can squeeze the proximal end of the button cap near to the latch member 60. This squeezing action causes the latch member 60 to pivot and the member 60a to disengage from the groove 56a located in the wall of the main body 56. The cap assembly may thus be separated from the main body. Providing a pivotable latch that needs to be squeezed is advantageous since it prevents unwanted removal of the cap assembly, for example by a child.

While cooperating circumferential grooves and ridges have been described above, in alternative embodiments discrete cooperating bumps and recesses may be provided instead around the circumference of the button cap 51, carrier unit 54 and main body 56. The positioning and design of the raised bumps and recesses may be selected depending on the best plastic moulding possibilities.

While embodiments of the disclosure have been described with respect to auto-injectors, it should be borne in mind that the disclosure is also applicable to alternative injection devices, for example syringes, pen-injectors, manual injectors, spinal injection systems etc. The mechanism for attaching the needle to the medicament cartridge may be employed in any injection device where it is desirable to keep the needle separate from the medicament until shortly before the injection.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15$^{th}$ edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten. An example of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A medicament injection device comprising:
a main body configured to receive a medicament cartridge sealed by a first penetrable barrier;
a cap assembly comprising a button cap and a carrier unit, wherein the button cap is dimensioned to fit over the carrier unit, the button cap being rotatable with respect to the carrier unit, and wherein the button cap is prevented from being displaced axially in a proximal direction unless the button cap is rotated into alignment with respect to the carrier unit; and
a needle carrier releasably coupled to the cap assembly, the needle carrier carrying a needle having a proximal end and a distal end,
wherein subsequent to rotational alignment of the button cap with respect to the carrier unit, the button cap is axially displaceable in the proximal direction,
wherein axial displacement of the button cap in the proximal direction causes the needle carrier to be displaced axially in the proximal direction, and
wherein subsequent to axial displacement of the button cap in the proximal direction, the button cap and the carrier unit of the cap assembly are separable from the main body and from the needle in a distal direction.

2. The device of claim 1, further comprising a medicament cartridge holder configured to hold the medicament cartridge, the medicament cartridge holder comprising a fixing part for fixing the needle carrier to the medicament cartridge subsequent to axial displacement of the needle carrier in the proximal direction.

3. The device of claim 1, wherein the button cap and the carrier unit each have alignment marks thereon to provide an indication of rotational alignment of the button cap with respect to the carrier unit.

4. The device of claim 1, wherein the carrier unit comprises a pivotable latch arranged to release the cap assembly from the main body of the device upon actuation.

5. The device of claim 1, wherein the button cap comprises a bore configured to receive the distal end of the needle, and wherein the carrier unit comprises a bore configured to receive the proximal end of the needle prior to axial displacement of the button cap.

6. The device of claim 5, wherein the bore which is configured to receive the proximal end of the needle is sealed at a proximal end thereof by a second penetrable barrier.

7. The device of claim 1, wherein the button cap and the carrier unit comprise a locking arrangement configured so that, subsequent to axial displacement of the button cap with respect to the carrier unit, the button cap and the carrier unit are fixed with respect to each other.

8. The device of claim 7, wherein the locking arrangement comprises at least one protruding member and at least one respective cooperating recess located on respective surfaces of the button cap and the carrier unit.

9. The device of claim 1, comprising the medicament cartridge sealed by the first penetrable barrier, wherein axial movement of the needle carrier in the proximal direction causes the proximal end of the needle to pierce the first penetrable barrier.

10. The device of claim 9, wherein the medicament cartridge contains a medicament.

11. The device of claim 1, wherein the device is an auto-injector device.

12. The device of claim 1, wherein subsequent to axial displacement of the button cap in the proximal direction, the button cap and the carrier unit of the cap assembly are separable from the main body in the distal direction such that the needle carrier is released from the cap assembly.

13. The device of claim 1, wherein the button cap is rotatable with respect to the carrier unit and the main body.

14. The device of claim 1, wherein axial displacement of the button cap in the proximal direction causes the needle carrier to be displaced axially in the proximal direction relative to the carrier unit.

15. A method of operating a medicament injection device having a cap assembly, the method comprising:
    rotating a button cap into alignment with a carrier unit, wherein the button cap is dimensioned to fit over the carrier unit;
    displacing the button cap in a proximal axial direction with respect to the carrier unit, thereby causing a needle to penetrate a cartridge septum; and
    subsequent to displacing the button cap in the proximal axial direction, removing both the button cap and the carrier unit of the cap assembly from the medicament injection device and from the needle by pulling the cap assembly in a distal axial direction opposite to the proximal axial direction.

16. The method of claim 15, further comprising actuating a pivotable latch to release the cap assembly from a main body of the medicament injection device.

17. The method of claim 15, wherein rotating the button cap into alignment with the carrier unit comprises aligning respective alignment marks provided on the button cap and the carrier unit.

18. The method of claim 15, wherein removing the button cap and the carrier unit from the medicament injection device causes the needle carrier is released from the cap assembly.

19. The method of claim 15, wherein displacing the button cap in the proximal axial direction causes the needle carrier to be displaced axially in the proximal direction relative to the carrier unit.

* * * * *